(12) United States Patent
Lubock et al.

(10) Patent No.: US 8,326,401 B2
(45) Date of Patent: Dec. 4, 2012

(54) MRI DETECTABLE OBTURATOR

(75) Inventors: Paul Lubock, Laguna Niguel, CA (US); Michael L. Jones, San Clemente, CA (US); Ethan Broadaway, Cordova, TN (US); Frank R. Louw, Carlsbad, CA (US)

(73) Assignee: Senorx, Inc., Tempe, AZ (US)

( * ) Notice: Subject to any disclaimer, the term of this patent is extended or adjusted under 35 U.S.C. 154(b) by 1415 days.

(21) Appl. No.: 11/985,997

(22) Filed: Nov. 19, 2007

(65) Prior Publication Data

US 2008/0139928 A1 Jun. 12, 2008

Related U.S. Application Data

(63) Continuation-in-part of application No. 11/978,782, filed on Oct. 30, 2007, and a continuation-in-part of application No. 11/980,302, filed on Oct. 30, 2007.

(60) Provisional application No. 60/860,887, filed on Nov. 24, 2006, provisional application No. 60/872,020, filed on Nov. 30, 2006.

(51) Int. Cl.
*A61B 5/05* (2006.01)

(52) U.S. Cl. ........ 600/420; 600/431; 600/414; 600/434; 600/435

(58) Field of Classification Search .......... 600/407–435, 600/562–568
See application file for complete search history.

(56) References Cited

U.S. PATENT DOCUMENTS

| | | | |
|---|---|---|---|
| 3,844,272 A | 10/1974 | Banko | |
| 4,989,608 A | 2/1991 | Ratner | |
| 5,800,389 A | 9/1998 | Burney et al. | |
| 5,845,646 A | 12/1998 | Lemelson | |
| 6,220,248 B1 | 4/2001 | Voegele et al. | |
| 6,238,355 B1 * | 5/2001 | Daum | 600/567 |
| 6,628,982 B1 | 9/2003 | Thomas et al. | |
| 6,939,318 B2 | 9/2005 | Stenzel | |
| 7,347,829 B2 | 3/2008 | Mark et al. | |
| 7,693,567 B2 * | 4/2010 | Tsonton et al. | 600/411 |
| 7,862,517 B2 * | 1/2011 | Tsonton et al. | 600/567 |
| 2005/0277829 A1 * | 12/2005 | Tsonton et al. | 600/423 |
| 2006/0036165 A1 | 2/2006 | Burbank et al. | |
| 2006/0241385 A1 * | 10/2006 | Dietz | 600/415 |
| 2007/0167736 A1 * | 7/2007 | Dietz et al. | 600/411 |
| 2008/0015429 A1 * | 1/2008 | Tsonton et al. | 600/414 |
| 2009/0281453 A1 * | 11/2009 | Tsonton et al. | 600/567 |

FOREIGN PATENT DOCUMENTS

| | | |
|---|---|---|
| EP | 1 114 618 | 7/2001 |
| FR | 2 853 521 | 4/2003 |
| WO | WO 02/41786 | 5/2002 |
| WO | WO 03/105940 | 12/2003 |
| WO | WO 2005/013832 | 2/2005 |
| WO | WO 2007/069105 | 6/2007 |
| WO | WO 2008/016551 | 2/2008 |

OTHER PUBLICATIONS

International Search Report for PCT/US2007/024255 mailed Jul. 22, 2008.
Written Opinion of the International Searching Authority for PCT/US2007/024255 mailed Jul. 22, 2008.

* cited by examiner

*Primary Examiner* — Sanjay Cattungal

(57) ABSTRACT

An obturator with an elongated shaft, a proximal end, a substantially closed distal end and a MRI detectable distal shaft portion, which does not interfere with magnetic resonance imaging of tissue proximate thereto. Preferably, the distal shaft portion has an effective MRI detectable mass so as to provide a clear, T1-weighted image within an outline of the distal shaft portion upon magnetic resonance imaging.

23 Claims, 3 Drawing Sheets

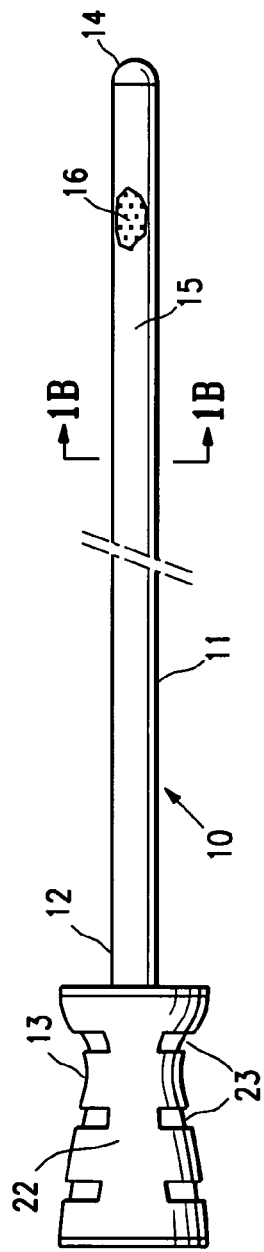
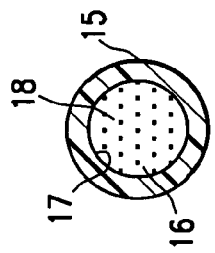
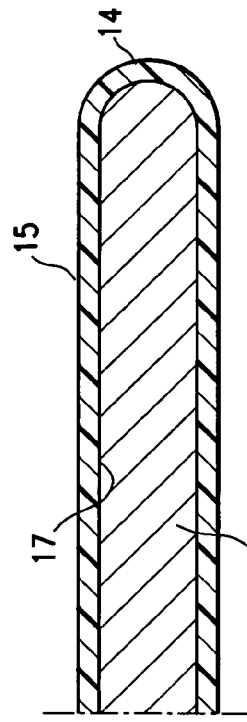
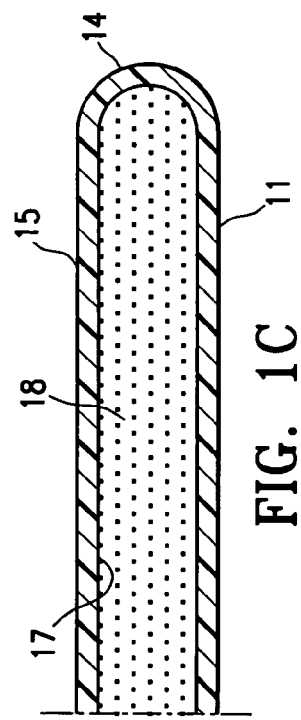
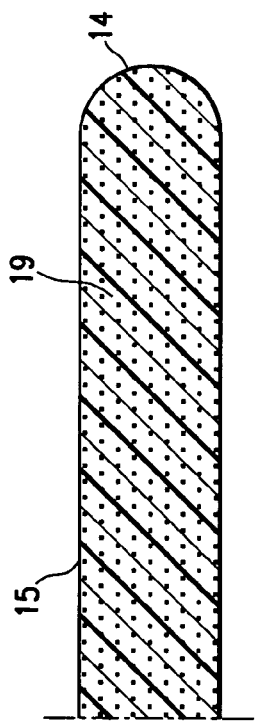

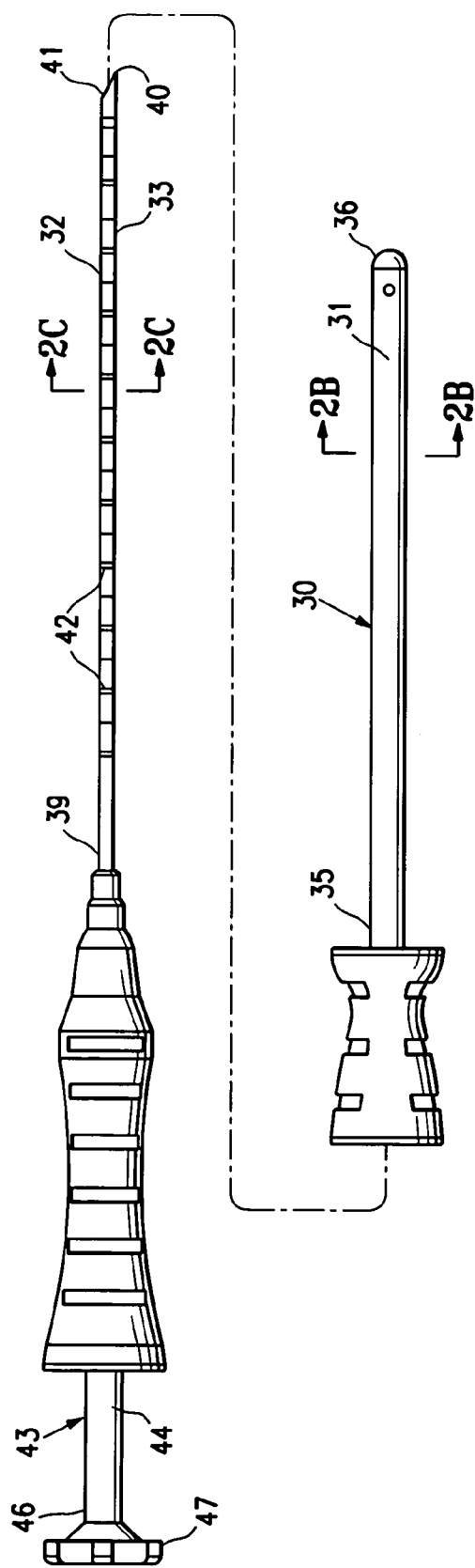
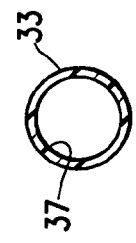
FIG. 2A
FIG. 2B
FIG. 2C

MRI DETECTABLE OBTURATOR

RELATED APPLICATIONS

This application is a continuation-in-part of application Ser. No. 11/978,782 filed Oct, 30, 2007, application Ser. No. 11/980,302, filed Oct. 30, 2007, provisional application Ser. No. 60/860,887, filed Nov. 24, 2006, and provisional application Ser. No. 60/872,020, filed Nov. 30, 2006, all of which are incorporated herein by reference and from which priority is claimed.

FIELD OF THE INVENTION

This invention relates generally to the fields of medical treatment devices and methods. In particular, the invention relates to devices and methods for marking a body site, such as a site from which cancerous, pre-cancerous, or other tissue has been or will be removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

A radiation source such as a miniature or micro-miniature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. Other inflatable treatment delivery devices and systems may be used to treat cancer in tissue adjacent a body cavity.

When performing an image guided biopsy procedure an obturator is used as a place holder and is located in tissue so that its distal tip will be located at the point in the patient's body where the biopsy is to be taken or where a biopsy site marker or tissue marker is to be placed after a biopsy procedure. Subsequent images are acquired that can confirm the correct placement of the obturator. When the obturator is placed at the desired location within the body, blood can enter the lumen of the obturator prior to delivery of the tissue markers. This backflow of blood into the obturator creates a risk of blood clotting.

Current obturators are constructed of homogeneous materials. During magnetic resonance imaging (MRI) guided biopsies, the tip of the obturator is located by indexing through many cross sectional views (typically every 2 mm, but higher and lower discriminations are possible). The material of the obturator will be distinguishable in the cross sectional images to a varying degree depending on the morphology of the tissue and the obturator's own material makeup. Since the prior obturators were homogeneous, the signature of the obturators will not vary from one cross-sectional image to the next along its length. The tip of the obturator is located by selecting the first cross-sectional image in which the obturator is not seen. This result can be visually ambiguous depending on the relative strength of the image signature of the obturator compared to the surrounding tissue.

SUMMARY OF THE INVENTION

This invention is generally directed to marking a patient's body cavity or other intracorporeal site (hereinafter collectively referred to as a body cavity) and devices and methods for such marking. The invention is particularly suitable for marking an intracorporeal site of a lesion by magnetic resonance imaging (MRI).

More specifically, the invention is directed to an obturator with an elongated shaft having a distal shaft portion which is detectable by MRI but which does not significantly interfere with imaging of an adjacent tissue, particularly an adjacent lesion. Preferably, the distal shaft portion of the obturator contains or has incorporated therein an MRI detectable agent in amounts effective to provide a readily apparent T1 MRI image within the outline of the distal shaft portion of the obturator.

The obturator having features of the invention operates as a place-holder during an MRI guided procedure such as a biopsy. The distal end of the obturator is placed where the procedure is to be performed or one or more intracorporeal objects or bodies are to be delivered.

In one embodiment having features of the present invention the device includes an obturator which has an elongated shaft with a internal lumen, a proximal end, and a substantially sealed distal end which prevents or minimizes the backflow of body fluids, such as blood, though the lumen of the obturator. The substantially sealed distal end can be a penetratable membrane or may have petals or a duckbill-type valve which are configured to allow passage of one or more intracorporeal objects or a delivery tube with one or more intracorporeal objects therethrough while preventing or minimizing entry of body fluids into the inner lumen of the obturator. Preferably, the obturator is configured to fit within a procedure cannula, e.g. a cannula of a biopsy device, for example, the cannula of SenoRx's EnCor™ Magnetic Resonance Imaging Breast Biopsy System. The cannula provides access to the desired location within the patient's body.

The delivery tube has a delivery lumen configured to contain one or more intracorporeal objects. The distal tip is configured to penetrate the substantially closed distal end of the obturator so that the intracorporeal bodies can be delivered while the obturator is in place within the body. The shape of the distal tip may be sharp or needle like when the distal end of the obturator has a pierceable membrane or it may be blunt or rounded when the distal end of the obturator is petalled or has a one-way valve.

The delivery tube preferably further includes a plunger having an elongated shaft with a proximal portion and a distal portion. The plunger is configured to be slidably disposed within the lumen of the delivery tube and is located proximal to the one or more intracorporeal objects within the lumen thereof. When the plunger is extended distally within the lumen, the distal end thereof moves one or more intracorporeal objects toward and eventually through the distal end of the delivery tube. The plunger preferably has an enlarged proximal end to prevent the distal portion of the plunger from advancing too far within the delivery lumen. Alternatively, a fluid maybe used to advance the intracorporeal objects through the opening in the distal end of the delivery tube.

A method for delivering one or more intracorporeal objects to a site within a patient's body includes providing the above described device. The obturator is placed at a desired location within a patient's body. The delivery tube is advanced distally within the obturator until the distal tip passes through the substantially closed distal end of the obturator. Next, the plunger is advanced distally within the delivery tube so that at least one intracorporeal object is pushed though the opening of the distal tip of the delivery tube.

The MRI detectable distal shaft portion of the obturator includes an MRI detectable mass which is capable of producing a significant image signature at the location in the patient's body where the distal portion of the obturator is placed without interfering with the imaging of adjacent tissue. In one embodiment the distal shaft portion has an MRI detectable material incorporated into a preferably solid distal shaft portion. In another embodiment the distal shaft portion has an inner portion or lumen filled with an MRI detectable mass. For example, an inner lumen extending within the distal shaft portion is filled with a gel having an MRI detectable material incorporated therein or filled with a solid MRI detectable element. The distal shaft portion has an effective amount of MRI detectable material so as to provide a clear, T1-weighted image within an outline of the distal shaft portion upon magnetic resonance imaging thereof.

The obturator embodying features of the invention may be used with a trocar assembly which has a trocar with a tissue penetrating distal tip and an introducer or trocar sheath which remains at the site after the trocar is removed. The introducer or trocar sheath may be similar to the split sheath trocar introducer which is described in co-pending provisional application Ser. No. 60/964,079. As described therein the split sheath may have a short cylindrical distal portion that is configured to provide a friction fit with the trocar proximal to the tissue penetrating distal tip. Preferably, the slit in the introducer sheath extends proximally from the cylindrical distal portion and widens in the proximal direction. The short cylindrical distal portion of the sheath preferably has a weakened or scored portion in alignment with the slit so that when the trocar is removed and an another instrument having a transverse dimension or expandable to a transverse dimension slightly larger than the internal transverse dimension of the short cylindrical sheath portion, the cylindrical section will tear or break to facilitate the removal of the sheath without removal of the instrument.

These and other advantages of the present invention are described in more detail in the following written description and the accompanying exemplary drawings.

BRIEF DESCRIPTION OF THE DRAWINGS

FIG. 1A is an elevational view of an obturator having features of the invention.

FIG. 1B is a transverse cross sectional view of the obturator of FIG. 1A taken along line 1B-1B.

FIG. 1C is a longitudinal cross sectional view of the obturator of FIG. 1A taken along lines 1C-1C.

FIG. 1D is a longitudinal cross sectional view of an alternative obturator with a gel filled distal shaft portion similar to the view shown in FIG. 1C.

FIG. 1E is a longitudinal cross sectional view of another alternative obturator with a solid filled distal shaft portion similar to the view shown in FIG. 1C.

FIGS. 2A-2C illustrate a marker delivery assembly which includes the obturator shown in FIG. 1.

DETAILED DESCRIPTION OF EMBODIMENTS OF THE INVENTION

Figure 2D:
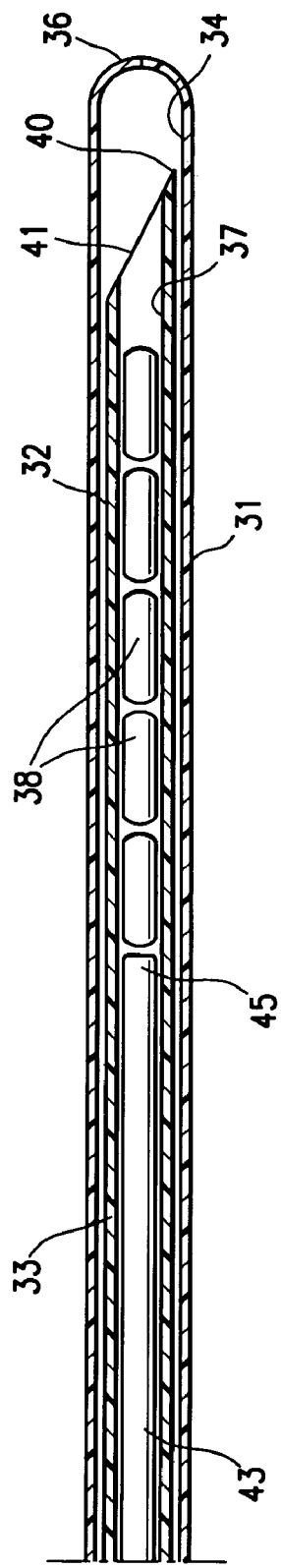
FIG. 2D is a longitudinal cross-sectional view of the distal portion of the assembly with the elements assembled.

The present invention is directed to devices and methods for marking an intracorporeal site within a patient's body, and particularly to an obturator having an MRI detectable mass in the distal shaft portion thereof for marking the intracorporeal site.

FIGS. 1A-C illustrate an embodiment of an obturator 10 having an elongated shaft 11, a proximal end 12, a handle 13 on the proximal end, a closed distal end 14 and a distal shaft portion 15 with an MRI detectable mass 16. The MRI detectable mass may be in a solid, semi-solid, e.g. a gel or a slurry, or liquid state. Non-flowable gels are presently preferred. As shown in FIGS. 1B and 1C, the distal shaft portion 15 has an inner lumen 17 that is filled with a gel 18 having an MRI detectable material incorporated therein. An alternative embodiment is shown in FIG. 1D wherein the distal shaft portion 15 is solid 19 and has an MRI detectable material incorporated therein. FIG. 1E depicts yet another alternative embodiment in which the distal shaft portion 15 has an inner lumen 17 that has a solid stylet 20, preferably formed of MRI detectable metallic material and preferably removable. The handle 13 has an outer surface 22 which facilitates gripping by the operator. In the embodiment shown, the outer surface is provided with a plurality of recesses 23 for gripping purposes. Alternatively, the surface of the handle 13 can be provided with raised portions or a roughened or other high friction surface to facilitate gripping by the operator. The obturator 10 is configured to fit within the lumen of a conventional trocar sheath (not shown) or the lumen or guide of a split sheath introducer such as shown in co-pending application Ser. No. 60/946,079, filed on Aug. 9, 2007.

FIGS. 2A-2D shows an assembly having features of the invention including an obturator 30 with an MRI detectable distal shaft portion 31 and a marker delivery member 32 having a tubular shaft 33. The obturator 30 has an inner lumen 34, a proximal end 35 and a substantially closed distal end 36.

Figures 3, 4:
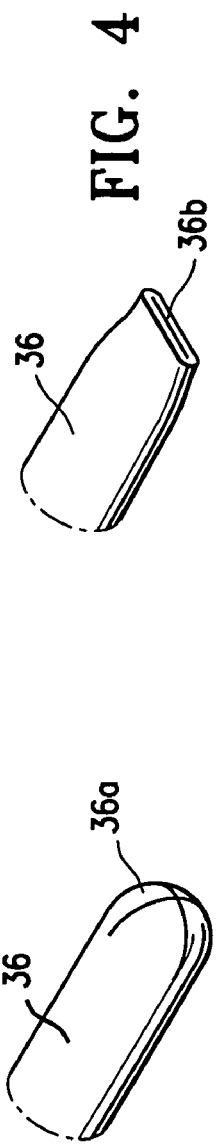
FIG. 3 is a perspective view of a substantially sealed distal end of an obturator having one or more petals.
FIG. 4 is a perspective view of a substantially sealed distal end of an obturator having a duck billed valve.

The distal shaft portion 31 preferably has a removable MRI detectable element (not shown) such as a stylet shown in FIG. 1E. The distal end 36 of the obturator 30 is substantially closed to prevent or minimize the backflow of fluids, such as body fluids, through the inner lumen 34 of the obturator. Preferably, the substantially closed distal end 36 is a penetratable membrane. Alternatively, the substantially closed distal end 36 is formed of two or more petals 36a (FIG. 3) or can be formed of a duck-billed valve 36b (FIG. 4).

The marker delivery tubular shaft 33 is configured to be slidably disposed within the internal lumen 34 of the obturator 30. The tubular shaft 33 has a marker delivery lumen 37 configured to contain one or more tissue markers 38 for marking a biopsy site, a proximal end 39, and a distal tip 40 with an opening 41 for passage of one or more of the markers 38. The tissue markers 38 may be those described in U.S. Pat. Nos. 6,996,433, 6,993,375, 6,862,470, 6,725,083, 6,662,041, 6,567,689, 6,427,081, 6,347,241, 6,161,034, U.S. patent application Ser. Nos. 10/444,770, 10/444,428, and 10/001,043. The marker delivery tubular shaft 33 preferably also includes depth markings 42 which indicate the distance which the tubular shaft 33 has advanced within the obturator 30.

The distal tip 40 of the marker delivery shaft 33 is configured to penetrate the substantially closed distal end 36 of the obturator 30 so that tissue markers 38 can be delivered while the obturator 30 is in place within the patient's body. Preferably the distal tip 40 is needle shaped as shown. However, the distal tip 40 can alternatively be a blunt tip which is capable of penetrating the distal end 36 that is formed of a penetratable membrane which is weakened or a distal end with petals 36a or a valve 36b as shown in FIGS. 3 and 4.

Preferably the marker delivery member 32 also includes a plunger 43 having an elongated shaft 44 with a distal end 45 and a proximal end 46. The plunger 43 is configured to be slidably disposed within the marker delivery lumen 37 and is located proximal to the one or more tissue markers 38 within the marker delivery lumen 37. When the plunger 43 is extended distally within the marker delivery lumen 37 it moves one or more tissue markers 38 toward and eventually through the opening 41 in the distal tip 40 of the marker delivery member. The plunger 43 preferably has an enlarged head 47 to facilitate manual advancement. Alternatively, a fluid (not shown) may be used to advance the markers 38 through the opening 41 in the distal tip 40 of the marker delivery member.

Preferably, the obturator 30 is configured to fit within a cannula of a biopsy device, such as SenoRx's EnCor™ Magnetic Resonance Imaging (MRI) Breast Biopsy System. The cannula provides access to the desired location within a patient's body.

Further details of this assembly are shown in provisional application Ser. No. 60/860,887, filed Nov. 24, 2006, and provisional application Ser. No. 60/872,020, filed Nov. 30, 2006. FIGS. 6A-6C show the distal tip 40 of the marker delivery tube 33 partially penetrating the substantially closed distal end 36 of the obturator 30. The tissue markers 38 are contained within the marker delivery lumen 37. FIGS. 6A-6C show the distal tip 40 completely penetrating the substantially closed distal end 36 of the obturator 30 and the tissue markers 38 within the marker delivery lumen 37. In operation, the plunger 43 is deployed distally within the marker delivery lumen 37 so that the distal end 45 engages the markers 38 and advances the markers out the opening 41.

The marker delivery member 32 is preferably formed of a non-magnetic material. A polymeric material such as MAKROLON®, a polycarbonate from Bayer Material Sciences a division of Bayer AG, is suitable and will not interfere with a magnetic resonance imaging device (MRI). The device may also include a radiopaque material which allows for radiographic detection of the device.

Positive MRI contrast agents cause a reduction in the T1 relaxation time (increased signal intensity on T1 weighted images). They appear bright on MRI and are typically small molecular weight compounds containing as their active element Gadolinium, Manganese, or Iron. All of these elements have unpaired electron spins in their outer shells and long relaxivities. Some typical contrast agents include $GdCl_3$, $Gd_2O_3$ gadopentetate dimeglumine (Gd-DPTA), Gd-EDTA, gadoteridol, gadoterate meglumine, mangafodipir trisodium and gadodiamide. Negative MRI contrast agents appearing predominantly dark on MRI are small particulate aggregates often termed superparamagnetic iron oxide (SPIO). These MRI contrast agents produce predominantly spin relaxation effects (local field inhomogeneities), which results in shorter T1 and T2 relaxation times. SPIO's and ultrasmall superparamagnetic iron oxides (USPIO) usually consist of a crystalline iron oxide core containing thousands of iron atoms and a shell of polymer, dextran, polyethyleneglycol, and produce very high T2 relaxivities. USPIOs smaller than 300 nm cause a substantial T1 relaxation. T2 weighted effects are predominant.

In one embodiment, a lumen in the distal shaft portion of the obturator is filled with a gel having an MRI contrast material. One suitable gel is mineral oil in plastisol. Another is a paramagnetic contrast agent in a hydrogel. For example, the following aqueous solutions were prepared at the indicated molar concentrations:

| MRI CONTRAST MATERIAL | MOLAR CONCENTRATION |
|---|---|
| Gadolinium Sulfate | 0.00002-0.0005 |
| Ferric Chloride | 0.00005-0.0005 |
| Ferrous Gluconate | 0.00005-0.001 |
| Manganese Chloride | 0.0001-0.0005 |

The aqueous solutions were mixed with polyvinyl alcohol cross-linked with boric acid to create a gel which is slightly flowable and less susceptible to bubble movement due to changes in position. Other gel forming materials include polyethylene glycol, gelatin, agar, polyHEMA, polyacrylamide, Pluronic F127. The formed gels need sufficient water to allow the water to react to the magnetic field during magnetic resonance imaging. To minimize loss of water during storage and the like, the gel may be protected with a material such as polypropylene which has essentially no water vapor transmission therethrough.

If an imagable stylet is used within the inner lumen of the obturator as shown in FIG. 1E, it is preferably formed of material which is compatible with MRI and which is seen in MRI generated images without interfering with imaging of adjacent tissue. Suitable materials include non-magnetic metals, non-magnetic metal filled plastics, hollow tubes filled at least in part with an MRI visible substance such as described above.

While particular forms of the invention have been illustrated and described herein directed to detectable markers, it will be apparent that various modifications and improvements can be made to the invention. For example, the deployed bodies may be therapeutic or diagnostic agents in addition to or in lieu of being markers. Moreover, individual features may be shown or otherwise described in one embodiment and not in others, but those skilled in the art will recognize that individual features of one embodiment of the invention can be combined with any or all the features of another embodiment. Accordingly, it is not intended that the invention be limited to the specific embodiments illustrated. To the extent not otherwise disclosed herein, materials and structure may be of conventional design.

Terms such as "element", "member", "component", "device", "means", "portion", "section", "steps" and words of similar import when used herein shall not be construed as invoking the provisions of 35 U.S.C §112(6) unless the following claims expressly use the terms "means for" or "step for" followed by a particular function without reference to a specific structure or a specific action. All patents and all patent applications referred to above are hereby incorporated by reference in their entirety.

What is claimed is:

1. An obturator for marking an intracorporeal site comprising an elongated shaft, a proximal end, a distal end, and an MRI detectable distal shaft portion which does not interfere with magnetic resonance imaging of tissue proximate thereto, the distal shaft portion having an effective amount of MRI detectable agent so as to provide a clear, T1-weighted image within an outline of the distal shaft portion upon magnetic resonance imaging thereof, the distal shaft portion having an inner lumen and the MRI detectable agent being contained in an MRI detectable gelled mass within the inner lumen, the MRI detectable gelled mass being formed of an aqueous solution of a MRI contrast agent mixed with a hydrogel, with the MRI contrast agent selected from the group consisting of Gadiolinium Sulfate, Ferric Chloride and Ferrous Gluconate, and the aqueous solution has a concentration of the MRI contrast agent of at least 0.00002 molar.

2. The obturator of claim 1 wherein the group further consists of Gadolinium, Manganese, and Iron.

3. The obturator of claim 1 wherein the group further consists of $GdCl_3$, $Gd_2O_3$ gadopentetate dimeglumine (Gd-DPTA), Gd-EDTA, gadoteridol, gadoterate meglumine, mangafodipir trisodium and gadodiamide.

4. The obturator of claim 1 wherein the distal end is closed.

5. The obturator of claim 4 wherein the closed distal end is a penetratable membrane.

6. The obturator of claim 4 wherein the closed distal end of the obturator is formed of one or more petals.

7. The obturator of claim 4 wherein the closed distal end of the obturator is a valve.

8. The obturator of claim 1, comprising a marker delivery member disposed within the inner lumen.

9. The obturator of claim 8 wherein the marker delivery member has a delivery lumen with one or more markers within the delivery lumen and a plunger slidably disposed within the delivery lumen and which is located proximal to the one or more markers.

10. The obturator of claim 9 wherein the proximal end of the plunger is enlarged.

11. The obturator of claim 9 wherein the marker delivery member has a needle shaped distal tip.

12. The obturator of claim 9 wherein the marker delivery tubular member has a blunt distal tip.

13. The obturator of claim 9 wherein the marker delivery shaft has depth markings.

14. The obturator of claim 9 wherein the proximal end of the obturator has a hub and the proximal end of the marker delivery member has a hub which is configured to fit within the hub of the obturator when the marker delivery shaft is inserted into the elongated shaft of the obturator.

15. The obturator of claim 9 wherein the marker delivery lumen contains a fluid proximal of the at least one tissue marker to facilitate discharge of the markers.

16. An obturator for marking an intracorporeal site comprising an elongated shaft, a proximal end, a distal end, and an MRI detectable distal shaft portion which does not interfere with magnetic resonance imaging of tissue proximate thereto, the distal shaft portion having an effective amount of MRI detectable agent so as to provide a clear, T1-weighted image within an outline of the distal shaft portion upon magnetic resonance imaging thereof, the distal shaft portion having an inner lumen and the MRI detectable agent being contained in an MRI detectable gelled mass within the inner lumen, the MRI detectable gelled mass being formed of an aqueous solution of a MRI contrast agent mixed with a hydrogel, with the MRI contrast agent selected from the group consisting of Gadiolinium Sulfate, Ferric Chloride and Ferrous Gluconate, and a molar concentration of the MRI contrast agent is at least 0.00005 molar.

17. The obturator of claim 16 wherein the proximal end of the obturator has a hub, wherein the hub of the obturator has gripping ridges.

18. The obturator of claim 17, comprising a marker delivery member disposed within the inner lumen, the marker delivery member having a marker delivery tubular shaft with a hub, wherein the hub of the marker delivery tubular shaft has gripping ridges.

19. The obturator of claim 16 wherein the obturator shaft is formed of a non-magnetic material.

20. The obturator of claim 16 wherein the obturator shaft is formed of a polymeric material.

21. The obturator of claim 20 wherein the polymeric material is a polycarbonate.

22. The obturator of claim 16 wherein the obturator shaft is configured to be used within a cannula of a biopsy device.

23. The obturator of claim 22 wherein the cannula has depth markings.

* * * * *